United States Patent
Mande et al.

(10) Patent No.: US 11,488,687 B2
(45) Date of Patent: Nov. 1, 2022

(54) SYSTEM AND METHOD FOR IMPROVED ESTIMATION OF FUNCTIONAL POTENTIAL OF GENOMES AND METAGENOMES

(71) Applicant: Tata Consultancy Services Limited, Mumbai (IN)

(72) Inventors: Sharmila Shekhar Mande, Pune (IN); Swadha Anand, Pune (IN); Kuntal Kumar Bhusan, Pune (IN); Vineet Bhatt, Pune (IN); Anwesha Mohapatra, Pune (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 1151 days.

(21) Appl. No.: 15/841,477

(22) Filed: Dec. 14, 2017

(65) Prior Publication Data
US 2018/0181702 A1 Jun. 28, 2018

(30) Foreign Application Priority Data

Dec. 27, 2016 (IN) .............................. 201621044472

(51) Int. Cl.
*G16B 20/20* (2019.01)
*G16B 20/00* (2019.01)
*G16B 40/00* (2019.01)
*G16B 40/30* (2019.01)
*G06N 7/00* (2006.01)

(52) U.S. Cl.
CPC ............. *G16B 20/20* (2019.02); *G16B 20/00* (2019.02); *G16B 40/00* (2019.02); *G16B 40/30* (2019.02); *G06N 7/005* (2013.01)

(58) Field of Classification Search
None
See application file for complete search history.

(56) References Cited

PUBLICATIONS

Bose et al. PLoS One (vol. 10, No. 11 (2015):16 pages.*
Dudhagara et al. Genomics Proteomics Bioinformatics vol. 13 (2015):296-303.*
Huson et al. In Methods in Molecular Biology 856:Evolutionary Genomics, ed. Anisimova; Humana Press (2012): Chapter 17—Introduction to the Analysis of Environmental Sequences: Metagenomics with MEGAN:20 pages.*
Kowar et al. BMC Bioinformatics vol. 14 (2013):10 pages.*
Zhao, S. et al. (Oct. 2013). "Discovery of new enzymes and metabolic pathways using structure and genome context." *Nature*, vol. 502, No. 7473; pp. 693-702.
Teixeira, A.S. et al. "Spanning edge betweenness," *Eleventh Workshop on Mining and Learning with Graphs*, Aug. 11, 2013, Chicago. IL; 6 pages.
Sorokina, M. et al. (Nov. 2015). "A new network representation of the metabolism to detect chemical transformation modules," *BMC Bioinformatics*, vol. 16, No. 385; pp. 1-9.
Ogata, H. et al. (2000). "A heuristic graph comparison algorithm and its application to detect functionally related enzyme clusters," *Nucleic Acids Research*, vol. 28, No. 20; pp. 4021-4028.

* cited by examiner

*Primary Examiner* — Lori A. Clow
(74) *Attorney, Agent, or Firm* — Finnegan, Henderson, Farabow, Garrett & Dunner LLP

(57) ABSTRACT

A system and method for estimation of functional potential of pathways in genomes/meta-genomes is provided. Initially seed modules are identified and a multi-dimensional tag map is created. Further, pathway annotation is done using a novel 6Q annotation step. Hidden Markov Model (HMM) based search augmented with an analysis of gene context is used to refine the modules using a graph theory based approach. The method uses the multidimensional module tag map to build a backend knowledge base and use the same for an iterative literature search to verify the clustered organization of genes within a pathway. Finally, a score is assigned to compute the contribution of each pathway within the genome/meta-genome.

6 Claims, 11 Drawing Sheets

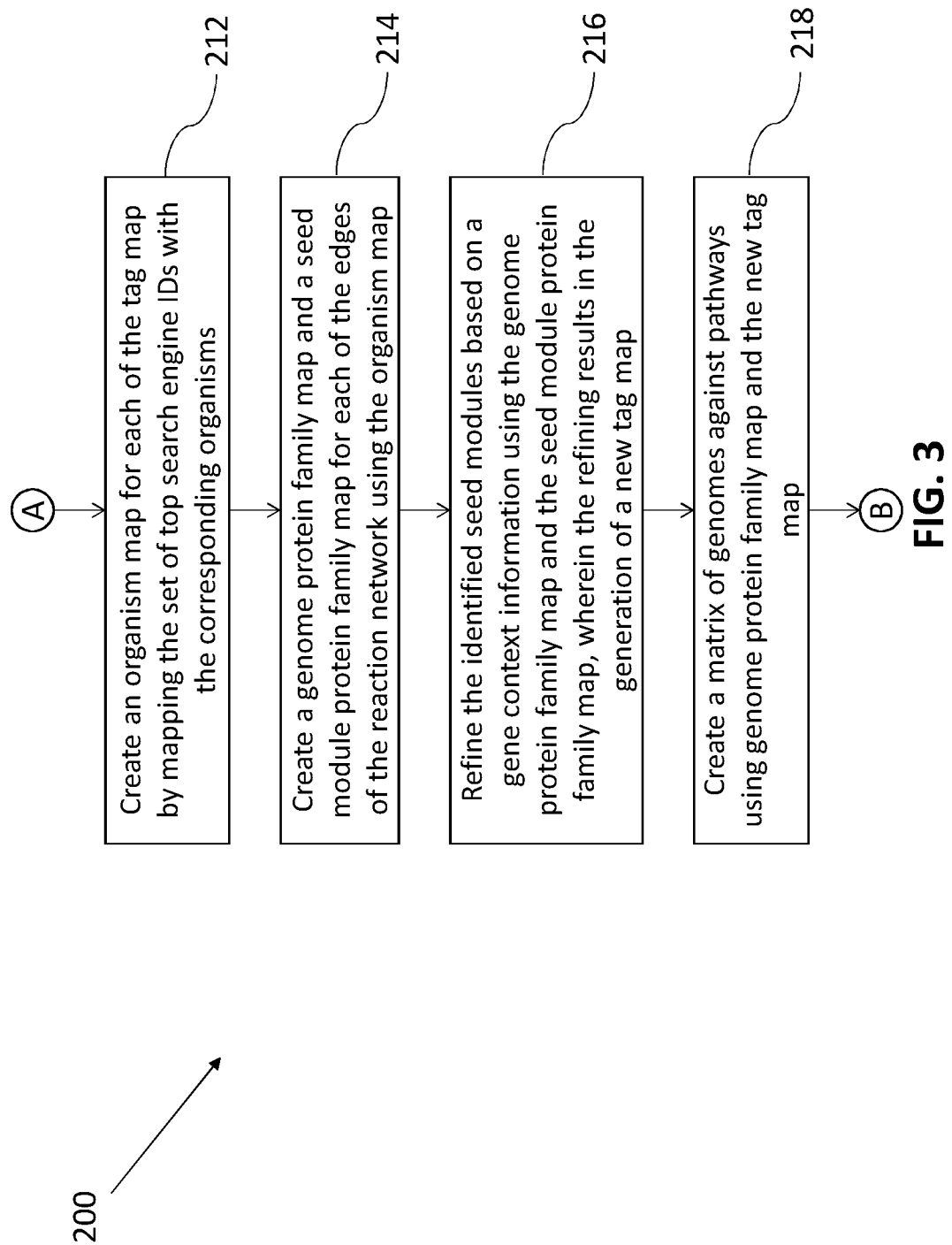

SYSTEM AND METHOD FOR IMPROVED ESTIMATION OF FUNCTIONAL POTENTIAL OF GENOMES AND METAGENOMES

CROSS-REFERENCE TO RELATED APPLICATIONS AND PRIORITY

The present application claims priority from Indian provisional specification no. 201621044472 filed on 27 Dec. 2016, the complete disclosure of which, in its entirety is herein incorporated by references.

TECHNICAL FIELD

The embodiments herein generally relates to the field of estimation of functional potential of genomes/metagenomes, and, more particularly, to a method and system for estimation of this functional potential using gene context information.

BACKGROUND

The microbial world is dominated by prokaryotic organisms, a majority of which are bacteria which inhabit diverse ecosystems ranging from aquatic, terrestrial, hot springs to various organs of the human body like skin, gut and lungs. Although 'micro' in size, the role played by these organisms is immense. Bacteria display the greatest range in metabolic ability ranging from decomposition of organic matter, cycling of nutrients in aquatic systems to shaping the host health. With emergence of metagenomics, the human microbiota has gained significant attention and enriched our knowledge of the resident microbes and their potential functional roles. The genetic material present in an environmental sample, consisting of the genomes of many individual organism (metagenome). The samples received can be analyzed to understand the functional potential of plurality of microbes comprising the microbiome. Understanding the functional potential of this resident micro-flora (estimated over 100 trillion) are expected to provide better insights in understanding the human physiology, metabolism, nutrition and immune function.

Functional potential primarily refers to the key metabolic pathways which are required for the maintenance of homeostasis within an organism or the ones required in breakdown and metabolism while obtaining nutrition from available resources. In a symbiotic environment like the human body, the meaning of functional potential further expands to the microbial community level where the resident species co-operate and co-inhibit each other in a complex manner. A metabolic pathway consists of a series of biochemical reactions connected by their intermediates where the products of one reaction are the substrates for subsequent reactions, and so on. The individual reactions are catalyzed by one or more enzymes with the help of co-factors. Every enzyme is product of a gene and often a multitude of genes are involved in synthesis of related group enzymes for a particular pathway. Owing to the relatively small genome real estate, the genes forming a pathway in bacterial genomes are usually not distributed randomly in the genome but are organized into groups of gene-clusters for improved efficiency. Subsequently, accurate characterization and quantification of such gene-clusters in a genome as well as a metagenome are quintessential to characterize the functional potential of a genome/metagenome.

Most of the current methods consider genes in isolation and link a phenotype to the presence of a set of genes or proteins. These methods often attribute these 'set of genes' to a pathway which may not actually be a pathway but merely a pool of statistically identified enriched set of genes. Majority of the current methods fail to account for the gene context or the relative order of the constituent genes of the pathway in the genome. Additionally, the criticality of the genes constituting a pathway is ignored by all existing methods which often lead to false positives. Improper annotation of existing pathways contributes to another major bottleneck in estimating the accurate functional potential.

SUMMARY

The following presents a simplified summary of some embodiments of the disclosure in order to provide a basic understanding of the embodiments. This summary is not an extensive overview of the embodiments. It is not intended to identify key/critical elements of the embodiments or to delineate the scope of the embodiments. Its sole purpose is to present some embodiments in a simplified form as a prelude to the more detailed description that is presented below.

In view of the foregoing, an embodiment herein provides a system for estimation of pathway based functional potential in genomes and metagenomes. The system comprises a public database, a memory and a processor. The public database provides a metabolic reaction knowledgebase. The metabolic reaction knowledgebase comprises compounds in pathways as nodes and reactions in pathways as edges. The processor is coupled with the memory. The processor is configured to perform the steps of: connecting the nodes and edges to create a reaction network; identifying a plurality of seed modules in the reaction network; creating a tag map for each of the identified seed modules represented by a module ID, wherein the tag map having a plurality of tag map values; providing a list of six queries to a biomedical literature search engine wherein the queries are generated using the plurality of tag map values, wherein the biomedical literature search engine results in the generation of a new list having a set of top search engine IDs and corresponding organisms; creating an organism map for each of the tag map by mapping the module ID with the corresponding organisms; creating a genome protein family map and a seed module protein family map using the organism map; refining the identified seed modules using the genome protein family map and the seed module protein family map, wherein the refining based on a gene context information results in the generation of a new tag map; creating a matrix of genomes against pathways using genome protein family map and the new tag map; creating a matrix of genomes against domains using genome protein family map; calculating a domain probability of occurrence of the domain in the refined seed module in the genome; and calculating a domain presence score, a domain skew index and a module probability score using the domain probability score to predict the functional potential of the pathways in the genome.

In another aspect, an embodiment provides a method for estimation of functional potential of pathways in genomes and metagenomes. Initially, a metabolic reaction knowledgebase from a public database is extracted. The metabolic reaction knowledgebase comprises compounds in pathways as nodes and reactions in pathways as edges. The nodes and edges are then connected to create a reaction network. A plurality of seed modules are then identified in the reaction network. In the next step a tag map is created for each of the identified seed modules represented by a module ID. The tag map having a plurality of tag map values. Further, a list of six queries is provided to a biomedical literature search engine wherein the queries are generated using the plurality of tag map values. The biomedical literature search engine results in the generation of a new list having a set of top search engine IDs and corresponding organisms. In the next step an organism map is created for each of the tag map by mapping the module ID with the corresponding organisms. And a genome protein family map and a seed module protein family map is created using the organism map. In the next step, the identified seed modules are refined using the genome protein family map and the seed module protein family map. The refining based on a gene context information results in the generation of a new tag map. At the next step, a matrix of genomes against pathways is created using genome protein family map and the new tag map. A matrix of genomes against domains is also created using genome protein family map. Further, a domain probability of occurrence of the domain in the refined seed module in the genome is calculated. And finally, a domain presence score, a domain skew index and a module probability score is calculated using the domain probability score to predict the functional potential of the pathways in the genome.

In another embodiment, a non-transitory computer-readable medium having embodied thereon a computer program for estimation of functional potential of pathways in genomes and metagenomes. Initially, a metabolic reaction knowledgebase from a public database is extracted. The metabolic reaction knowledgebase comprises compounds in pathways as nodes and reactions in pathways as edges. The nodes and edges are then connected to create a reaction network. A plurality of seed modules are then identified in the reaction network. In the next step a tag map is created for each of the identified seed modules represented by a module ID. The tag map having a plurality of tag map values. Further, a list of six queries is provided to a biomedical literature search engine wherein the queries are generated using the plurality of tag map values. The biomedical literature search engine results in the generation of a new list having a set of top search engine IDs and corresponding organisms. In the next step an organism map is created for each of the tag map by mapping the module ID with the corresponding organisms. And a genome protein family map and a seed module protein family map is created using the organism map. In the next step, the identified seed modules are refined using the genome protein family map and the seed module protein family map. The refining based on a gene context information results in the generation of a new tag map. At the next step, a matrix of genomes against pathways is created using genome protein family map and the new tag map. A matrix of genomes against domains is also created using genome protein family map. Further, a domain probability of occurrence of the domain in the refined seed module in the genome is calculated. And finally, a domain presence score, a domain skew index and a module probability score is calculated using the domain probability score to predict the functional potential of the pathways in the genome.

It should be appreciated by those skilled in the art that any block diagram herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and so executed by a computing device or processor, whether or not such computing device or processor is explicitly shown.

BRIEF DESCRIPTION OF THE DRAWINGS

The embodiments herein will be better understood from the following detailed description with reference to the drawings, in which.

The Figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION OF EMBODIMENTS

The embodiments herein and the various features and advantageous details thereof are explained more fully with reference to the non-limiting embodiments that are illustrated in the accompanying drawings and detailed in the following description. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Figure 1:
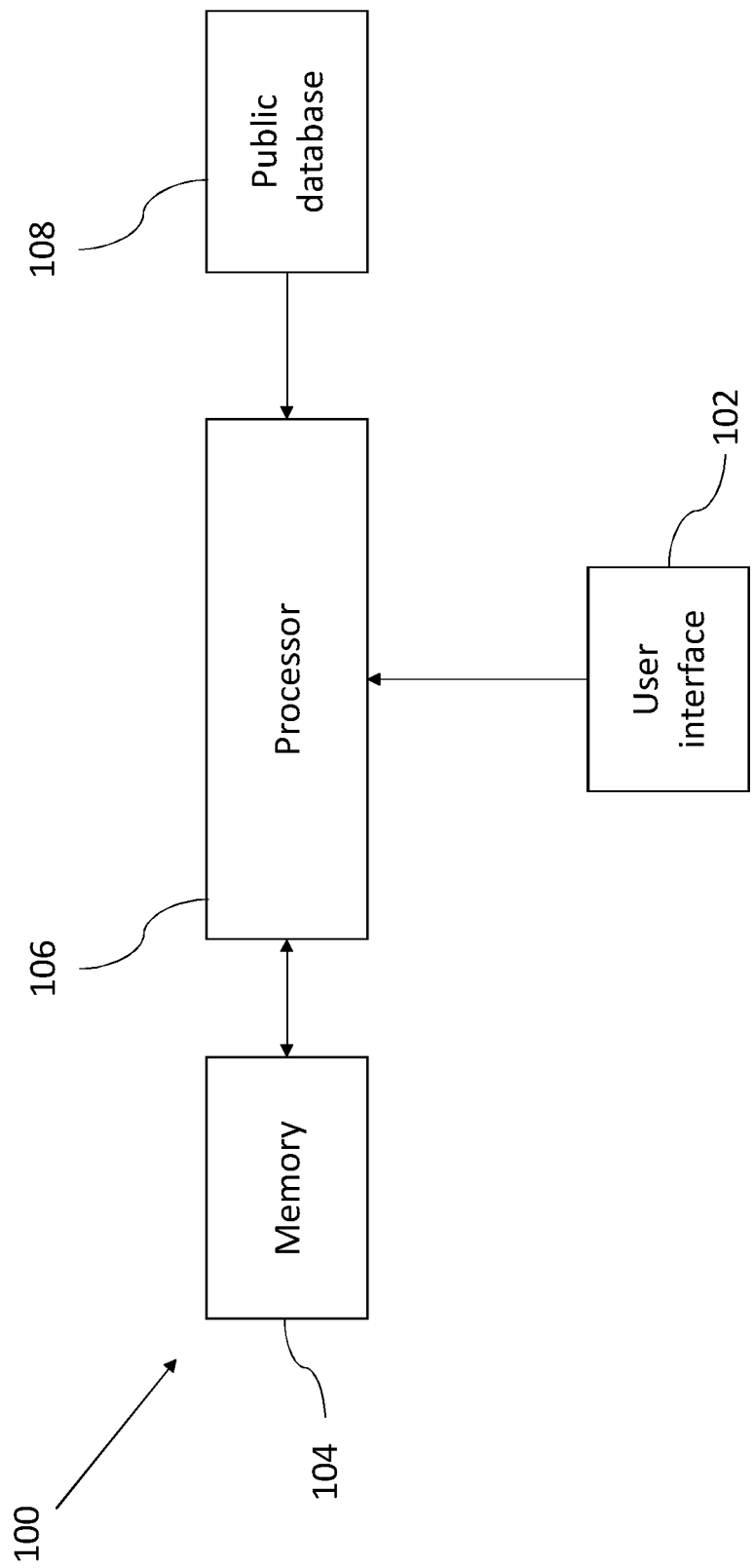
FIG. 1 illustrates a block diagram of a system for estimation of functional potential of pathways in genomes and metagenomes, in accordance with an embodiment of the present disclosure.

Referring now to the drawings, and more particularly to FIG. 1, where similar reference characters denote corresponding features consistently throughout the figures, there are shown preferred embodiments and these embodiments are described in the context of the following exemplary system and/or method.

According to an embodiment of the disclosure, a system 100 for estimation of functional potential of pathways in genomes/metagenomes is shown in the block diagram of FIG. 1. The system uses gene context information to estimate the functional potential of pathways. The disclosure provides a sophisticated pathway annotation using a set of innovative steps comprising of six query strings abbreviated as '6Q'. The disclosure uses a multidimensional module tag map to build a backend knowledge base and use it for an iterative literature search. Further, a Hidden Markov Model (HMM) based search is used to infer the gene context and refine the modules using a graph theory based approach. It should be appreciated that the use of any other model is well within the scope of this disclosure. Finally, a score is assigned to compute the contribution of each pathway within the genome/metagenome.

According to an embodiment of the disclosure, the system 100 comprises an input module 102 or user interface 102, a memory 104, a processor 106 and a public database 108 in communication with the memory 104 as shown in FIG. 1. The processor 106 configured to execute a plurality of algorithms stored in the memory 104. The processor 106 further includes a plurality of modules for performing various functions.

According to an embodiment of the disclosure, the system 100 receives metagenomic samples collected from different environments using the user interface 102. The samples received are then further analyzed to understand the functional potential of plurality of microbes comprising the microbiome. Functional potential primarily refers to the key metabolic pathways which are required for the maintenance of homeostasis within an organism or the ones required in breakdown and metabolism while obtaining nutrition from available resources. The user interface 102 may include a variety of software and hardware interfaces. The user interface 102 may allow the system 100 to interact with the user directly or through the client devices. The user interface 102 can facilitate multiple communications within a wide variety of networks and protocol types, including wired networks, for example, LAN, cable, etc., and wireless networks, such as WLAN, cellular, or satellite. The user interface 102 may include one or more ports for connecting a number of devices including assistive technology devices or adaptive products used by people with disability to one another or to another server.

According to an embodiment of the disclosure, the system 100 also includes a public database 108. A metabolic reaction knowledgebase is extracted from the public database 108. Normally a metabolic reaction involves reactants and products represented as compounds/metabolites involved in the reaction. The metabolic reaction knowledgebase comprises compounds involved in the pathways as nodes, while the reaction in the pathways as edges. In an example, a KEGG database has been used for extracting edge information. In another example, the system 100 might involve extraction of edge and node information using other pathway databases like PATRIC, BioCyc etc. The nodes and edges of a metabolic reaction network maybe in the form of 'XML' files or any other file in another embodiments. The nodes and edges are connected to create an undirected reaction network R.

According to an embodiment of the disclosure, the processor 106 is configured to identify a plurality of seed modules in the reaction network R. The reaction network R gives information about connections between the compounds which are used for creating the initial network. Most networks consist of modules which are densely connected themselves but sparsely connected to other modules. In an embodiment, the 'edge betweenness' score of an edge is used to measure the number of shortest paths through it. In this iterative process the edge betweenness is calculated, edge with the highest score is removed and the score is recalculated. In another embodiment, the 'Fastgreedy' method can also be used for identifying the plurality of seed modules '$M_1 \ldots M_n$'. The use of any other method for identifying a plurality of seeds is well within the scope of this disclosure.

Figure 6:
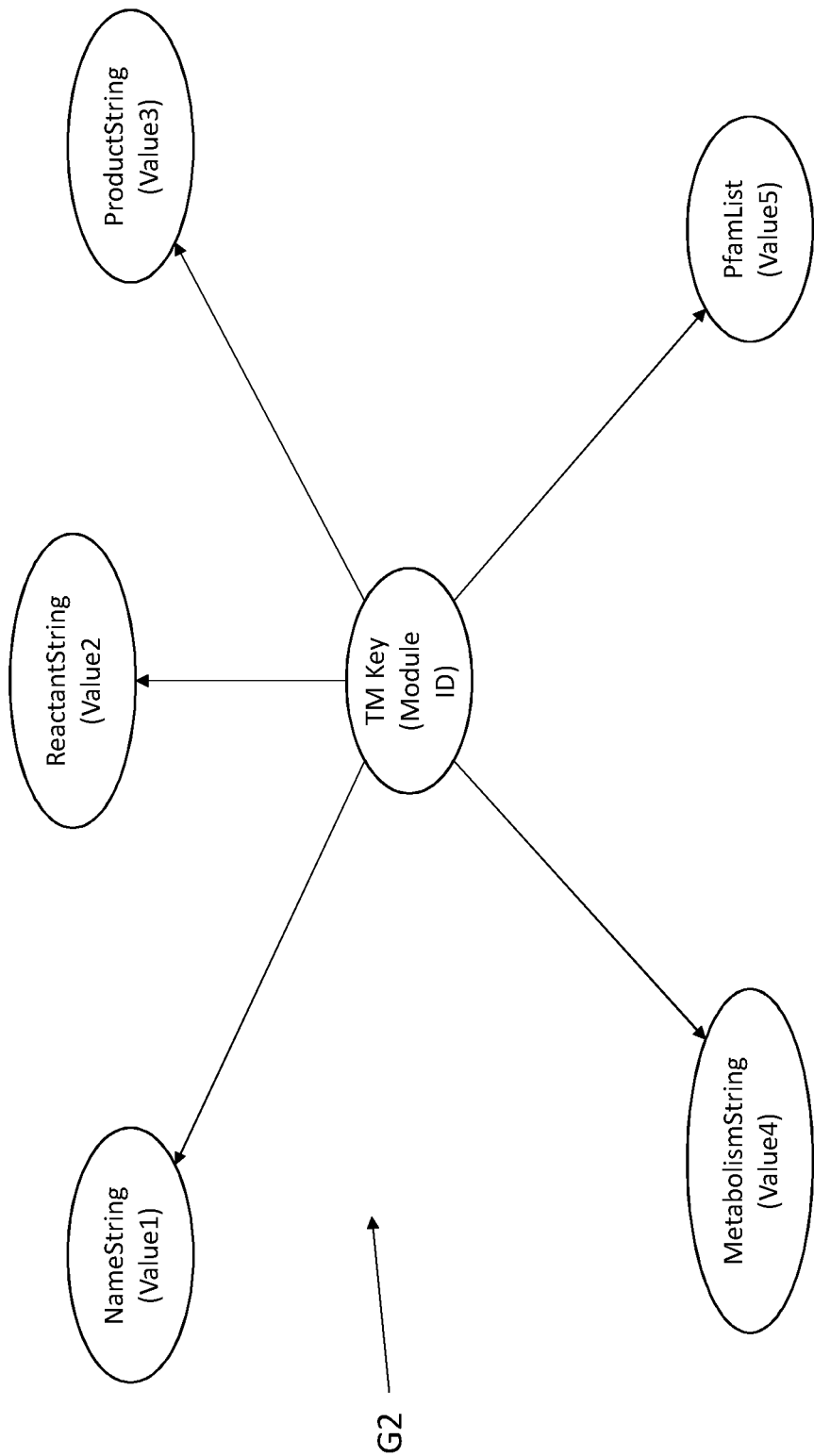
FIG. 6 shows the structure of tag map TM in accordance with an embodiment of the disclosure.

According to an embodiment of the disclosure, the processor 106 further configured to create a tag map (TM) for each of the identified seed modules represented by a module ID as shown in FIG. 6. The tag map is a multidimensional representation in the computer memory. It should be appreciated that each of the plurality of seed modules comprises a plurality of tag map values. In an embodiment, each entry of the tag map comprises of six values as follows. The first value is a unique alphanumeric ID for a module such as a 'TM_key'. The unique alphanumeric ID forms the primary identifier. The second value for the module as 'NameString'. The second value is a manually curated string identifier for a pathway module. The third value is for the module as 'ReactantString'. The third value is a manually curated string identifier for source metabolite/reactant. The fourth value is for the module as 'ProductString'. The fourth value is a manually curated string identifier for target metabolite/product. The fifth value is for the module as 'MetabolismString'. The fifth value is a manually curated string specifying Degradation (D)/Synthesis (S)/Metabolism (M). And the sixth value is for the protein family list or the Pfam list as 'PfamList'. The sixth value is an empty string whose values get populated at a later stage.

According to an embodiment of the disclosure, the processor 106 further configured to generate an organism map for each of the tag map. The system 100 further generates a list of six queries to a biomedical literature search engine corresponding to the plurality of tag map values corresponding to the tag map. In an embodiment, a total of six queries (Q1 to Q6) are generated for each of the unique alphanumeric ID. These queries are various permutation and combination of plurality of tag map values in addition to additional requirement. The list of six queries comprises:

a 'MetabolismString'+'ReactantString'+'ProductString' labeled as Q1, a 'MetabolismString+'ReactantString' labeled as Q2, a 'MetabolismString'+'ProductString' labeled as Q3, a 'MetabolismString'+'Reactanttring'+'ProductString'+'gene cluster' labeled as Q4, a 'MetabolismString'+'ReactantString'+'ProductString'+'bacteria' labeled as Q5 and a 'MetabolismString'+'ReactantString'+'ProductString'+'operon' labeled as Q6.

In an embodiment, a curated biomedical literature search engine such as PubMed is used. The use of any other search engine is well within the scope of this disclosure. The six queries Q1 to Q6 are provided as input to the search engine. The search engine provides output as six lists L1 to L6 of PubMed IDs corresponding to the six input queries. In each of the lists, the PubMed IDs are sorted by relevance for each query. Each list is then filtered to obtain the top 100 hits. Further, the consensus PubMed IDs with occurrences in at least four of the six lists are stored in a new list 'NL'. A pre-calculated mapping of PubMed IDs to the organisms is then created to generate a hash 'PO' with PubMed IDs as key and organism names as 'values'. Finally for every element in the list 'NL', the hash 'PO' is used to find the organism names mapped to each PubMed ID in the list 'NL'. The output organism names is stored in a new list 'OL', thus creating the organism map corresponding to the tag map. In another embodiment the searching can also be performed on other literature database such as Pubtator etc. with same Query approach.

According to an embodiment of the disclosure, the processor 106 further configured to create a genome protein family map and a seed module protein family map using the organism map.

The genome protein family map or the genome Pfam map is created as follows: initially a protein domain database 'PDM' is created. Any method present in the art can be used for that purpose. Further a database 'BGD' is created consisting of FASTA format protein sequences of bacterial genome with 'genome name' as primary identifiers (or keys) for each entry. Subsequently, a Hidden Markov model (HMM) based protein domain search (using HMMER in this implementation) on 'BGD' using 'PDM' as domain database is performed. Finally Pfams are obtained corresponding to each genome 'G' and a mapping hash 'GP' is created with 'key' as 'genome name' and 'value' as Pfam list 'PLG'. Each 'PLG' list is sorted based on corresponding gene locations. In the present embodiment, NCBI .ptt files were used as reference. In another embodiment, assignments may be done using other HMM databases like InterPro, SMART etc. or PSSM based databases like conserved domain database (CDD). In yet another embodiment, the genome context information can be obtained using any other bank or source such as Genbank file of a genome as reference too.

The seed module protein family map is created as follows. The corresponding Pfam IDs are obtained as a list 'PLM' for each edge of network created for each of the modules 'TM_key'. In an embodiment, the corresponding Pfam IDs are obtained from KGML. Finally, the sixth value of the hash 'TM' is updated with the list 'PLM' as obtained above.

Figure 2:
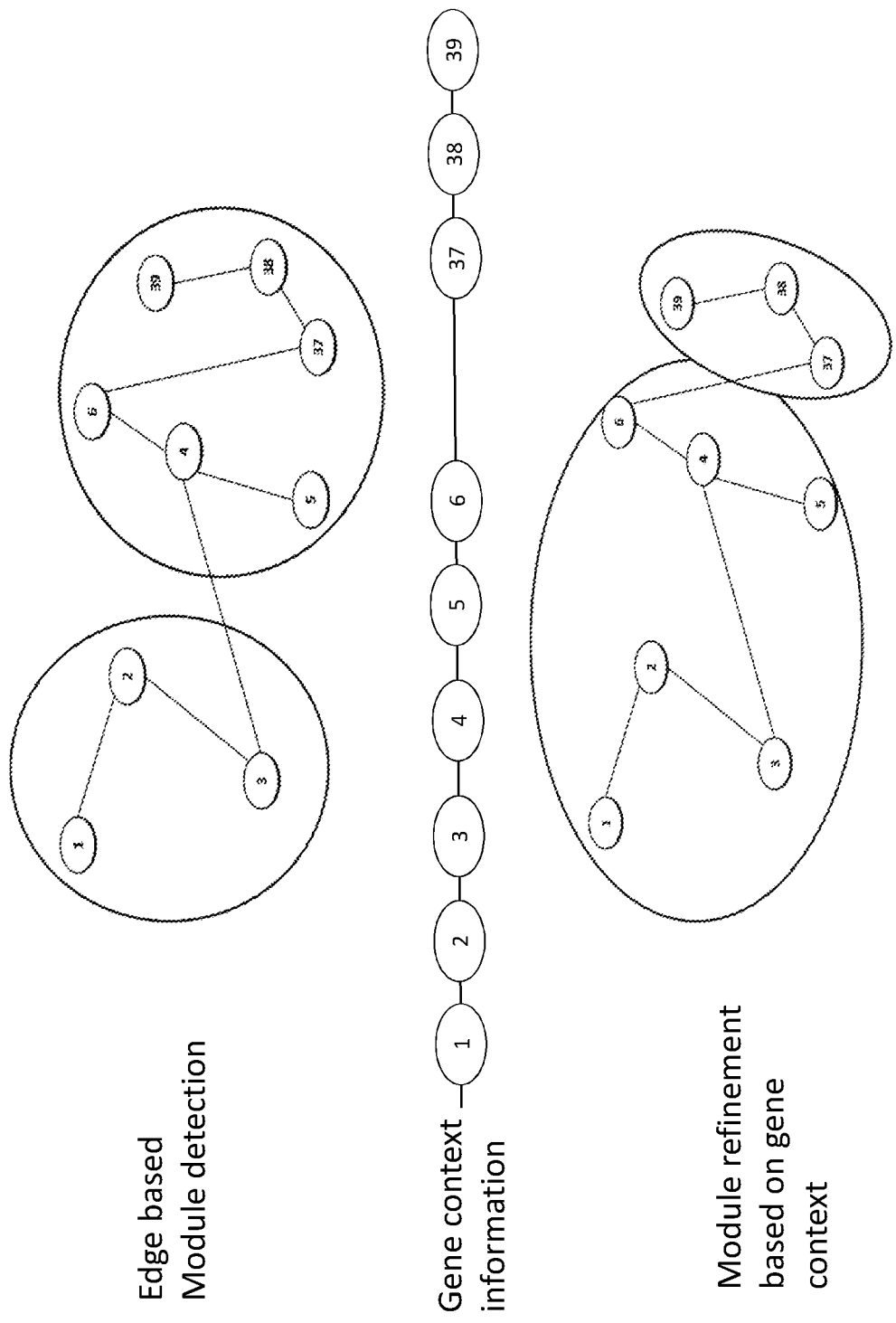
FIG. 2 shows a refinement of modules based on the gene context information, in accordance with an embodiment of the present disclosure.
Figure 3:
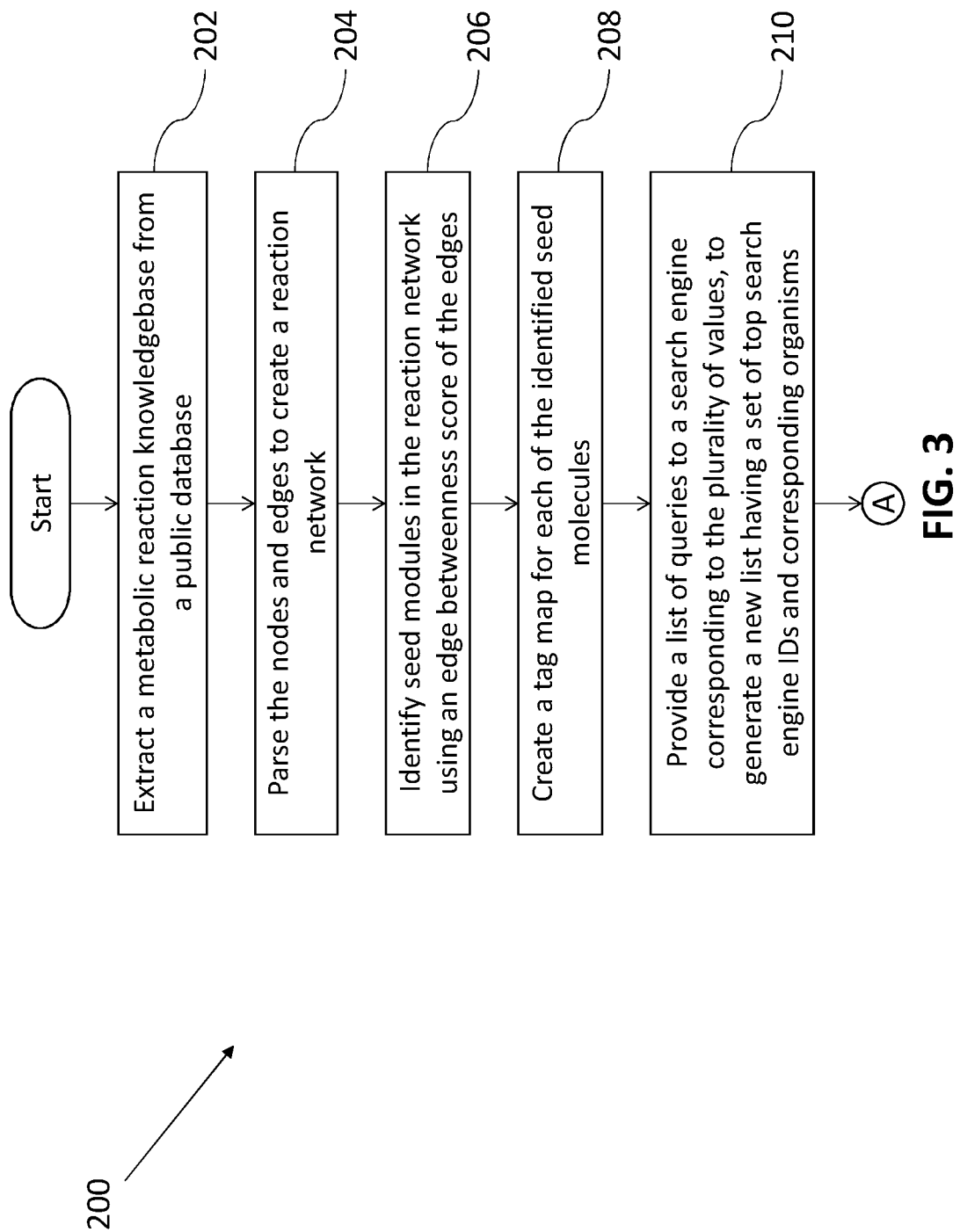
FIG. 3 is a flowchart illustrating the steps involved for estimation of functional potential of pathways in genomes and metagenomes, in accordance with an embodiment of the present disclosure.
Figure 3:
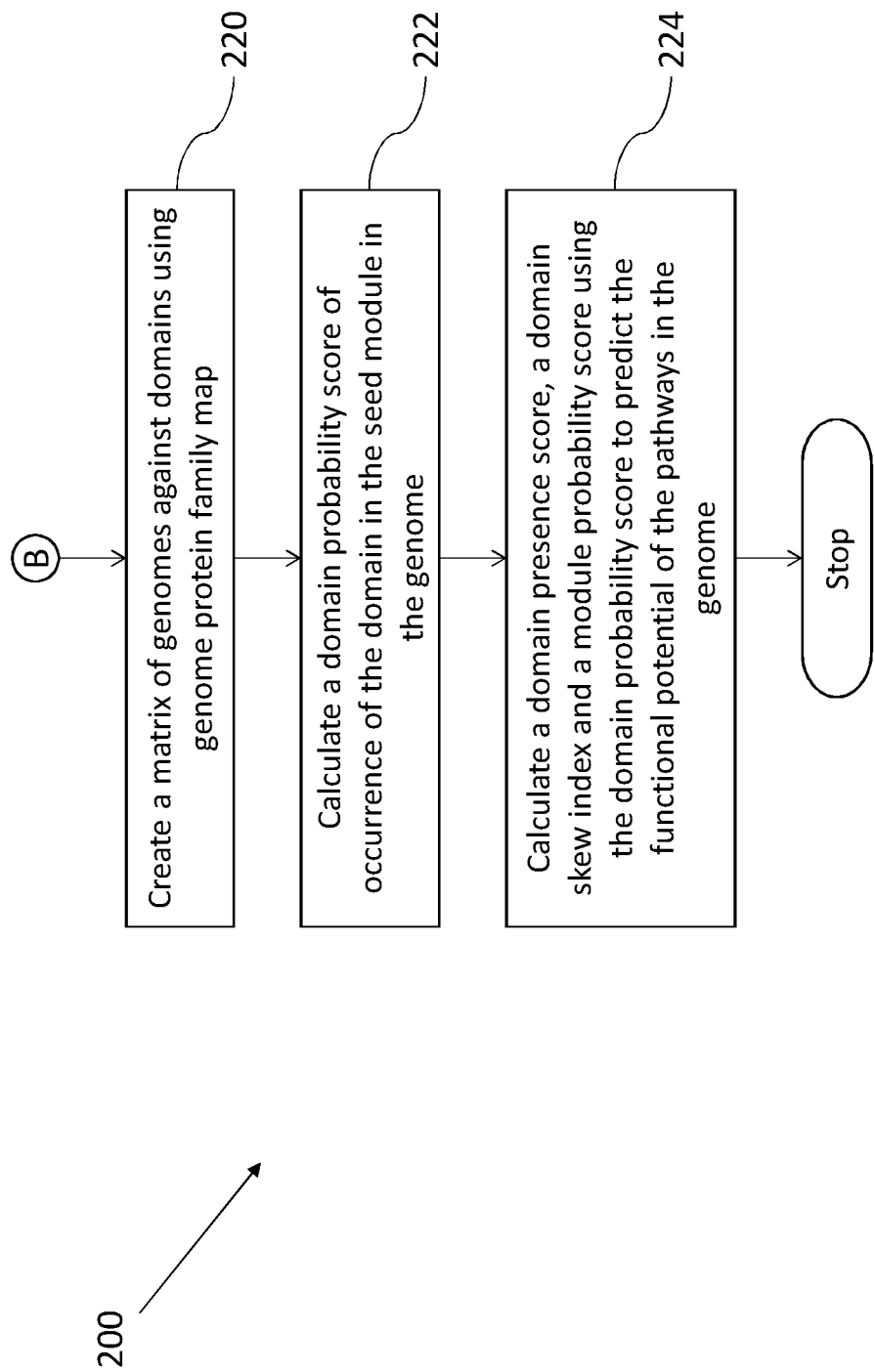

According to an embodiment of the disclosure, the processor 106 further configured to refine the identified seed modules as shown in the schematic representation of FIG. 2. The refinement is done based on gene context information using the genome protein family map and the seed module protein family map. The module contents corresponding to the fifth values ('PfamList') of 'TM' for each modules $M_1 \ldots M_n$ are identified. A location array 'LA' is created for 'PfamList' of each module using 'GP' as reference. In the next step all location arrays are merged into a single location array 'SLA' keeping only unique locations. Location clusters are then identified from 'SLA' separated not more than 10 genes. And finally, each new cluster is assigned as 'NewModuleID'. In the next step, a new multi-dimensional module tag map 'TM2' is created with 'NewModuleID' as key and following two values. The first value for the new modules as 'NewPfamList' (pfams constituting the new module). The second value for the new modules as 'OrganismList' ('OL' from one of the previous step). The 'OrganismList' comprises organisms which have the new module.

According to an embodiment of the disclosure, the processor 106 further configured to create a matrix of genomes against pathways using the genome protein family map and the new tag map. It should be appreciated that this referred pathway corresponds to our defined pathway and not a public pathway like KEGG. The genome protein family map is used to search for those organisms which have all the Pfams in the gene context. A matrix of Genome vs Pathways is then created for pathways $M_1 \ldots M_m$ and Genomes $G_1 \ldots G_n$. Similarly, a matrix of genomes against domains is created using genome protein family map. A mapping of pathways ('Key') to domains ('value' as list) and store it in hash 'PD'.

According to an embodiment of the disclosure, the processor 106 is also configured to calculate a functional potential of pathways in terms of three scores. The three scores are calculated using domain probability. The domain probability is referred as the probability of occurrence of $i^{th}$ domain 'D' in the seed module 'M' present in the genome 'G'. The domain probability is calculated using the formula shown below:

$$P_i^D = \frac{K}{\sum D_i}$$

Where,
K=1 if domain is found in context with other domains in the module
K=0 if domain is not found in context with other domains in the module or is absent in the genome.
$\Sigma D_i$ is the copy number of domain $D_i$ in genome 'G'

According to an embodiment of the disclosure, the three scores include domain presence score (DPS), domain skew index (DSI), and module probability score (MPS). The domain presence score is calculated using following formula:

$$DPS_M^G = \Sigma_{i=1}^n K$$

Where,
n=Total number of domains in a module 'M' in a genome 'G'
K=1 if domain is found in context with other domains in the module.
K=0 if domain is not found in context with other domains in the module or is absent in the genome.

The domain skew index is calculated using following formula:

$$DSI_G^D = \frac{\sum_G D_i}{\frac{\sum_{G=1}^J D_i}{J}}$$

Where,
J=Total number of genomes present in the database where $\Sigma D_i \neq 0$
$\Sigma_G D_i$ is the copy number of $i^{th}$ domain 'D' in genome 'G'.

The module probability score is calculated using following formula:

$$MPS_M^G = \prod_{i=1}^n \frac{P_i^D}{DSI_G^D}$$

Where,
n=Total number of domains in a module 'M' in genome 'G' for $P_i^D \neq 0$ In operation, a flowchart 200 illustrates the steps involved for estimation of functional potential of pathways in genomes and metagenomes. Initially at step 202, a metabolic reaction knowledgebase from the public database 108 is extracted. The metabolic reaction knowledgebase comprises multiple compounds and reactions. The compounds in pathways are referred as nodes and reactions in pathways are referred as edges. At step 204, the nodes and edges are connected to create a reaction network. At the next step 206, the plurality of seed modules are identified in the reaction network using an edge betweenness score of the edges. In an embodiment, a 'FastGreedy' method is used for identifying the plurality of seed modules.

At step 208 the multi-dimensional module tag map is created for each of the identified seed modules represented by a module ID. The tag map has the plurality of tag map values including the value for the primary identifier, the first value for string identifier for the pathway module, the second value for string identifier for source metabolite/reactant, the third value for string identifier for target metabolite/product, the fourth value for string specifying degradation/synthesis/metabolism and the fifth value for the Pfam list. At step 210, the list of six queries is provided to the biomedical literature search engine corresponding to the plurality of tag map values. The biomedical literature search engine results in the generation of a new list having a set of top search engine IDs and corresponding organisms. At step 212, the organism map is created for each of the tag map by mapping the module IDs with the corresponding organisms. At step 214, the genome protein family map and a seed module protein family map is created using the organism map.

At the next step 216, the identified seed modules are refined based on a gene context information using the genome protein family map and the seed module protein family map. The refining results in the generation of the new tag map. At step 218, a matrix of genomes against pathways is created using genome protein family map and the new tag map. The referred pathway corresponds to our defined pathway and not a public pathway like KEGG. At step 220, the matrix of genomes against domains is created using genome protein family map. At step 222, a domain probability score of occurrence of the domain in the seed module in the genome is calculated. And finally at step 224, the domain presence score, the domain skew index and the module probability score is calculated using the domain probability to predict the functional potential of the pathways in the genome.

According to an embodiment of the invention, the importance of gene context in the pathway prediction can be explained with the help of following example.

I. Importance of Gene Context in Pathway Prediction.

Figure 4:
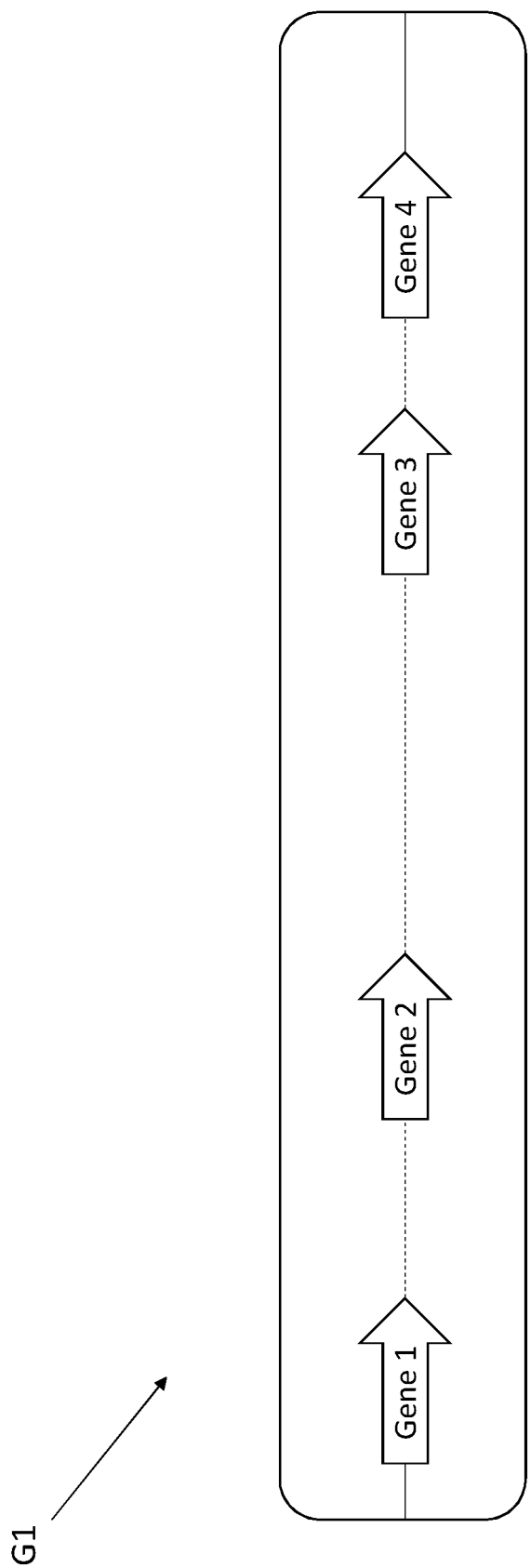
FIG. 4 shows depiction of genes in a pathway within genome G1 where pathway does not exist but homologs of constituent genes occur scattered on the genome in accordance with an embodiment of the present disclosure.
Figure 5:
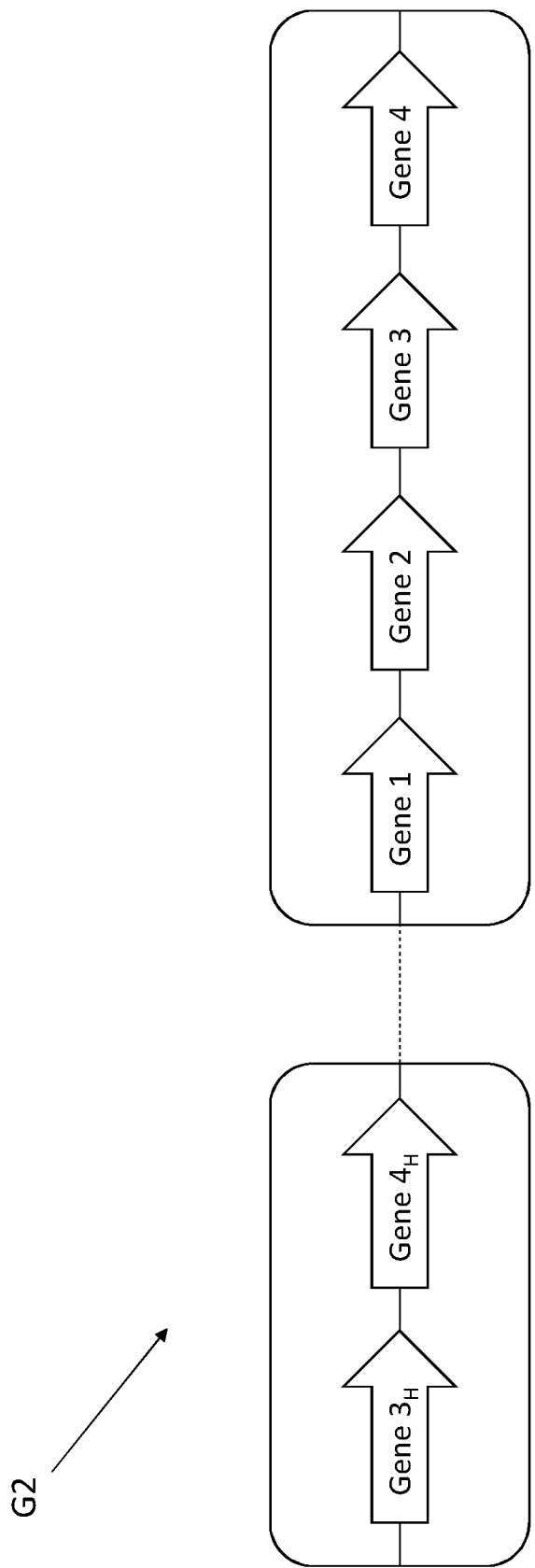
FIG. 5 shows depiction of genome G2 where existence of pathway P is experimentally verified and constituting genes form a cluster on the genome in accordance with an embodiment of the present disclosure.

An analysis involving augmentation of gene homology information with knowledge of genomic organization of genes constituting a pathway can help pick the genes actually forming the pathway and leave out other homologs which function in other pathways. FIGS. 4 and 5 depicts a case study wherein the occurrence of Genes 1, 2, 3, 4 that are constituents of pathway P in (a) Genome G1 which lacks the pathway and (b) Genome G2 which is experimentally proven to possess it. FIG. 4 shows that genome G1 contains homologs for all genes within this pathway but they are scattered on the genome probably functional in other pathways separately as shown with the help of dotted lines in the figure. A method not accounting for genome context will also annotate this mere presence of four genes on the genome as a pathway, which would give misleading results. The gene context based method used in the present disclosure will help to correctly rule out the presence of pathway P on genome G1 in agreement with experimental studies. On the contrary, FIG. 5 shows that in Genome G2 the genes of pathway P are arranged in a juxtaposed manner and form the actual pathway. The homologs of Gene 3 and Gene 4 occur elsewhere on the genome also but are not part of the pathway P under study. These homologs, which can bring about discrepant overestimation of copy number of a gene on the genome can also be removed out of calculation using genomic organization as an add-on.

IIa. Data Structure for TM_Key

The primary identifiers include 'TM_key' and 'NameString' which help in identification of the manually curated modules. The NameString comprises "ReactantString_ProductString". The ReactantString and ProductString identify the initial substrate and the final product of the corresponding module. MetabolismString indicates whether the module involves degradation of substrate/biosynthesis of product/metabolism. PfamList includes the HMM based PFAM assignments to each enzyme (edge of the network) connecting all intermediates between initial substrate and final product. In this example, the module includes four genes, which carry out biosynthesis ('Metabolism String') of GDP-L-Fucose ('ProductString' or final product) from Mannose-1-Phosphate ('ReactantString' or initial substrate). The pfam domains corresponding to these four genes have been listed in the column PfamList as shown in the table below:

| TM_key | NameString | ReactantString | ProductString | Metabolism String | PfamList |
|---|---|---|---|---|---|
| 00051 | Mannose-Fucose | Mannose-1-Phosphate | GDP-L-Fucose | Biosynthesis | PGM_PMM MannoseP_isomer GDP_Man_dehyd Epimerase |

IIb. Input for 6Q Approach and Module-Reference Organism Mapping

An explanation of how the 6 queries Q1 . . . Q6 were designed for input to literature search for creation of Module-Organism map taking same example as above.

Module here is 00051_Mannose-1-Phosphate_GDP-L-Fucose (TM_key_ReactantString_ProductString)
Biosynthesis+Mannose-1-Phosphate+GDP-L-Fucose
Biosynthesis+Mannose-1-Phosphate
Biosynthesis+GDP-L-Fucose
Biosynthesis+Mannose-1-Phosphate+GDP-L-Fucose+ 'gene cluster'
Biosynthesis+Mannose-1-Phosphate+GDP-L-Fucose+ 'bacteria'
Biosynthesis+Mannose-1-Phosphate+GDP-L-Fucose+ 'operon'

Using these 6 queries six lists of pubmed IDs L1 . . . L6 were obtained. The two pubmed IDs that occurred in 4 out of 6 lists included 1. 9473059

Paper reference: Identification of the fucosesynthetase gene in the colanic acid gene cluster of *Escherichia coli* K-12.J Bacteriol. 1998 February; 180(4):998-1001.

Mapped to organism *Escherichia coli*

Figure 7:
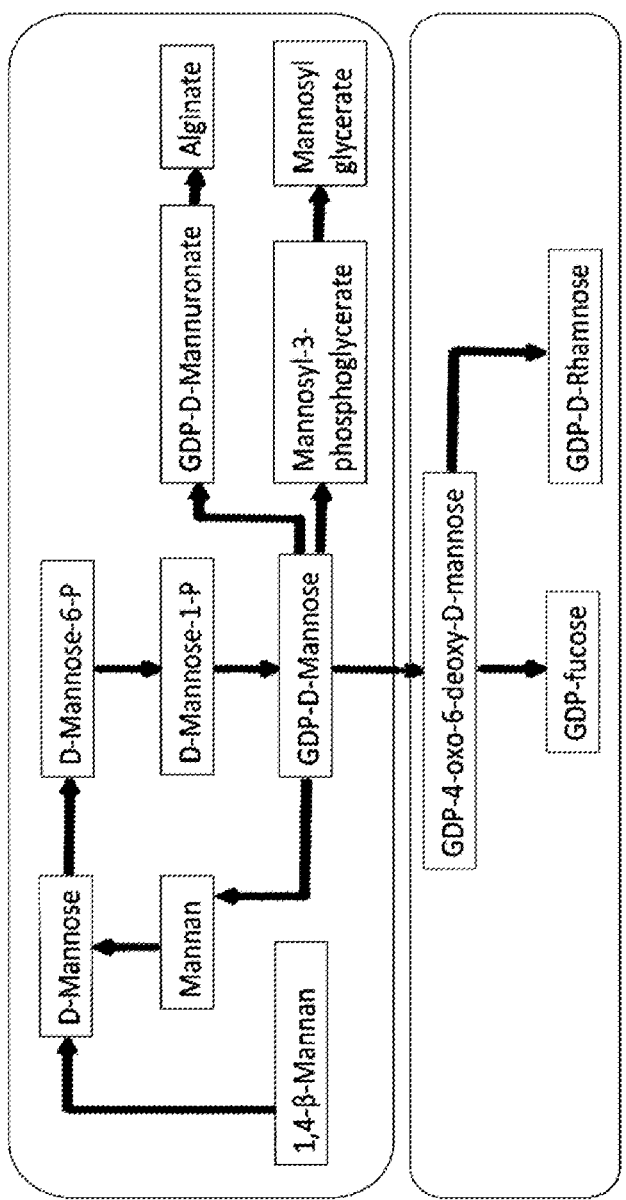
FIG. 7 depicts the identification of modules using fast greedy algorithm based on edge connectivity for mannose metabolism pathway in *Escherichia coli* as an example in accordance with an embodiment of the present disclosure.
Figure 8:
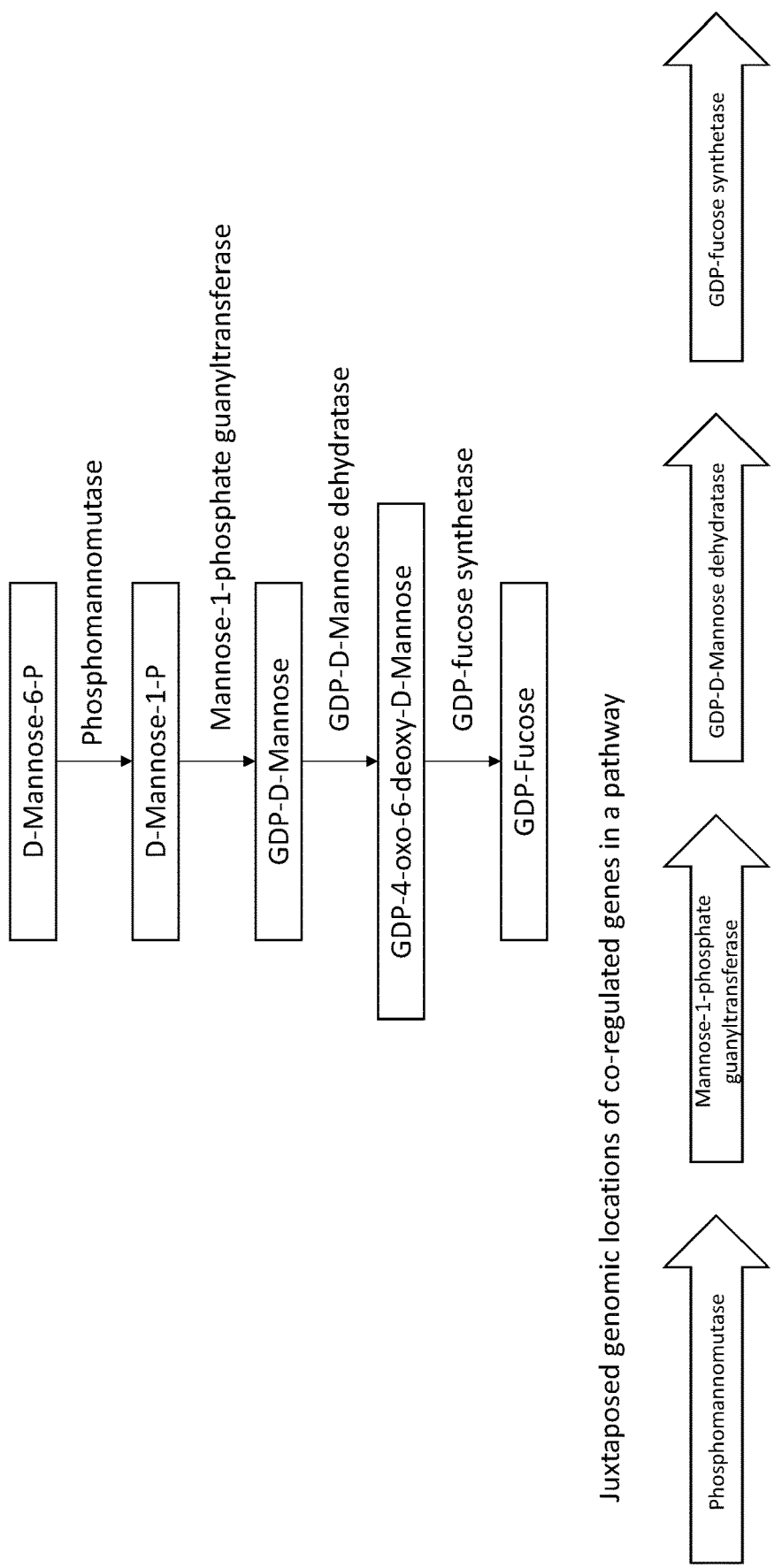
FIG. 8 depicts the importance of accounting for genome context in identifying correct functional modules in bacteria for the example used in FIG. 6, in accordance with an embodiment of the disclosure.

2. 8759852
Organization of the *Escherichia coli* K-12 gene cluster responsible for production of the extracellular polysaccharide colanicacid. J Bacteriol. 1996 August; 178(16):4885-93.
Mapped to organism *Escherichia coli*
Thus, *Escherichia coli* was used as a reference organism to create list 'OL' for module 00051_Mannose-1-Phosphate_GDP-L-Fucose IIc. Need and Procedure for Module Refinement The modules defined on the basis of edge connectivity's in KEGG might not always represent actual biological phenomena correctly. An example is depicted below where Mannose metabolism pathway is shown according to edge connections provided by KEGG. The problem with the assignments arises because all parts of this pathway are not observed in all organisms. KEGG depicts all the interactions known for each compound irrespective of the organism being considered. The mannan pathway is observed only in eukaryotes while GDP fucose formation pathway is a prokaryotic pathway. Alginate pathways are observed in only few genera in bacteria e.g. *Pseudomonas*. Thus, the modules defined using these connections only as the basis may mask the actual biological significance. The example shown here is for organism *Escherichia coli*, which is a bacteria lacking Mannan and alginate pathways. Therefore, these modules should further be refined in order to account for actual pathways in a given bacteria. As shown by literature search discussed earlier, the genes for conversion of Mannose to Fucose form evolutionarily conserved gene clusters in bacteria like *E. coli*. As shown in FIG. 7, inspite of experimental validation available for it being a sub-pathway, module definition just based on edge connections leads to dividing this pathway (Mannose-1-P to GDP-L-Fucose) into two separate modules. This discrepancy leads to loss of correct understanding of biological function. Thus, it becomes imperative to account for genomic location of genes within a pathway to obtain functionally viable modules as shown in FIG. 8. The genome context information will help to define modules on the basis of evolutionary conservation of genomic arrangements of pathways in their functional form. This information allows to account for actual physiological interactions in a bacteria and hence, are a better representation of functional potential of a bacteria.

Figure 9:
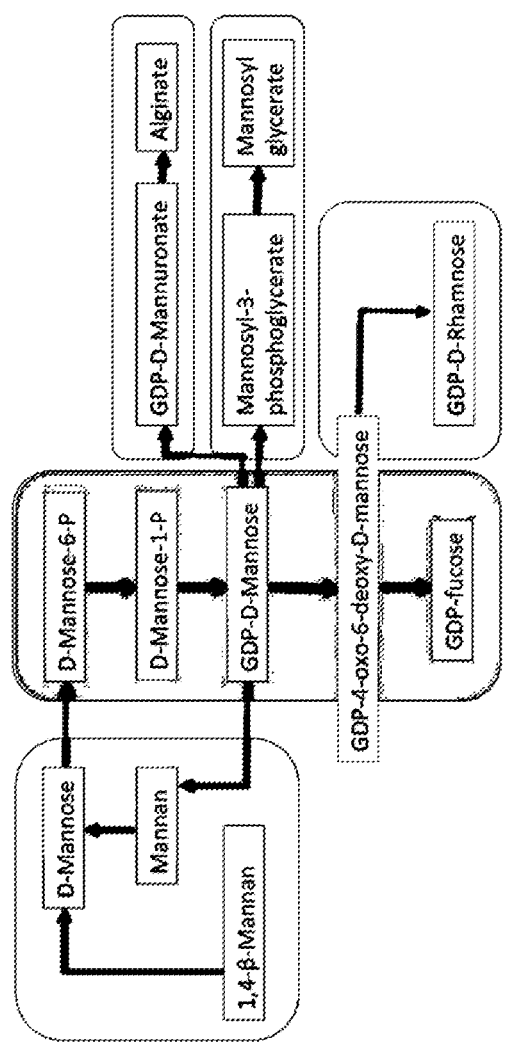
FIG. 9 depicts the new modules defined for the example used in FIG. 6 after the refinement in accordance with an embodiment of the present disclosure.

Including the genome context information for the pathway in addition to connectivity's lead to a complete redefinition of modules, thereby removing discrepancies in function prediction. The modules predicted after refinement with gene context information are shown below in FIG. 9. The genome context based module refinement defines new modules which have biological significance. The pathway from Mannose-6-phosphate to GDP-L fucose has been well characterized experimentally in bacteria and forms a gene cluster on genomes possessing this pathway. Similarly, the pathway for alginate production has also been shown to occur in clustered arrangement on the *Pseudomonas* genome. Thus, the modules defined after using genome context are in agreement with experimental findings in literature.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is, however to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

A representative hardware environment for practicing the embodiments may include a hardware configuration of an information handling/computer system in accordance with the embodiments herein. The system herein comprises at least one processor or central processing unit (CPU). The CPUs are interconnected via system bus to various devices such as a random access memory (RAM), read-only memory (ROM), and an input/output (I/O) adapter. The I/O adapter can connect to peripheral devices, such as disk units and tape drives, or other program storage devices that are readable by the system. The system can read the inventive instructions on the program storage devices and follow these instructions to execute the methodology of the embodiments herein.

The system further includes a user interface adapter that connects a keyboard, mouse, speaker, microphone, and/or other user interface devices such as a touch screen device (not shown) to the bus to gather user input. Additionally, a communication adapter connects the bus to a data processing network, and a display adapter connects the bus to a display device which may be embodied as an output device such as a monitor, printer, or transmitter, for example.

The preceding description has been presented with reference to various embodiments. Persons having ordinary skill in the art and technology to which this application pertains will appreciate that alterations and changes in the described structures and methods of operation can be practiced without meaningfully departing from the principle, spirit and scope.

What is claimed is:

1. A method for estimation of functional potential of pathways in genomes and metagenomes, the method comprising a processor implemented steps of:

extracting a metabolic reaction knowledgebase from a public database, wherein the metabolic reaction knowledgebase comprises of compounds in pathways as nodes and reactions in pathways as edges;

connecting the nodes and edges to create a reaction network;

identifying a plurality of seed modules in the reaction network by using connections between the compounds in the pathways as the nodes and the reactions in the pathways as the edges, wherein the plurality of seed modules are defined based on edge connectivity in the public database;

creating a tag map for each of the identified seed modules represented by a module ID, wherein the tag map is a multidimensional module map containing a plurality of tag map values, wherein the plurality of tag map values comprising an alphanumeric ID for the seed module, a name string identifier for pathway module, a reactant string identifier for source reactant, a product string identifier for target product, a metabolism string identifying a type of reaction and a protein family list;

providing a list of six queries to a biomedical literature search engine, wherein the list of six queries are generated using the plurality of tag map values, wherein the list of six queries comprise a metabolism string+reactant string+product string, a metabolism string+reactant string, a metabolism string+product string, a metabolism string+reactant string+product string+'gene cluster', a metabolism string+reactant string+product string+'bacteria' and a metabolism string+reactant string+product string+'operon', wherein the six queries are generated for each of the alphanumeric ID, wherein the biomedical literature search engine provides search output as six lists (L1 to L6) of publication IDs corresponding to the six queries;

sorting each of the six lists based on relevance to each query and selecting a predefined number of entries from each list to create a new list;

creating a pre-calculated mapping of the publication IDs to corresponding organisms to generate a hash 'PO' with the publication IDs as key and organism names as 'values' and identifying the organism names corresponding to each publication ID from the new list by using the hash PO;

creating an organism map by storing the organism names corresponding to the each publication ID in the new list thereby mapping the module ID with the corresponding organisms;

creating a genome protein family map and a seed module protein family map using the organism map, wherein the creation of the genome protein family map comprises:

performing Hidden Markov Model (HMM) based protein domain search on a protein database comprising protein sequences of genome;

obtaining protein family (Pfams) list corresponding to each genome 'G' and a mapping hash 'GP' created with 'key' as 'genome name' and 'value' as the Pfam list; and wherein the creation of seed module protein family map comprises the steps of:

obtaining a list for each edge of the reaction network created for each of the plurality of seed modules corresponding to a protein family;

obtaining a corresponding protein family IDs from the metabolic reaction knowledgebase; and updating the protein family list from the plurality of tag map values with the protein family IDs so obtained;

refining the identified plurality of seed modules using the genome protein family map and the seed module protein family map to generate a new tag map, wherein the refining comprises:

obtaining the protein family list for each of the plurality of seed modules and creating a location array for each protein family list for each of the plurality of seed modules using the mapping hash 'GP' as a reference;

merging all the location arrays into a single location array 'SLA' keeping only unique locations;

identifying location clusters from the 'SLA' separating a predefined number of genomes;

assigning each cluster a new module and creating the new tag map for the new module ID using the new module ID as a key and two values including the protein family list corresponding to the new module ID and organism list corresponding to the new module ID;

creating a matrix of genomes against pathways and a matrix of genomes against protein domains using genome protein family map and the new tag map, wherein the matrix of genomes against pathways and the matrix of genomes against the protein domains are mapped, wherein the genome protein family map is used to search for the organisms which have all the protein family (Pfams) of the module in a gene context, wherein the gene context refers to relative order of constituent genes of the pathway in the genome organized into groups of gene-clusters, and wherein the genomes and the protein domains are obtained from the genome protein family map;

calculating a domain probability of occurrence of the domain in the refined seed module in the genome; and calculating a domain presence score, a domain skew index and a module probability score using the domain probability score to predict the functional potential of the pathways in the genome, wherein the functional potential of the pathways in the genome is used to gain insights in understanding at least one of human physiology, metabolism, nutrition and immune function.

2. The method of claim 1 wherein the gene context information required for refining the identified seed modules is obtained using NCBI .ptt or Genbank file of a genome as reference tool.

3. The method of claim 1, wherein the public database is at least one of a KEGG, PATRIC or BioCyc.

4. The method of claim 1, wherein the biomedical literature search engine is PubMed.

5. A system for estimation of functional potential of pathways in genomes and metagenomes, the system comprising:
    a public database for providing a metabolic reaction knowledgebase, wherein the metabolic reaction knowledgebase comprises compounds in pathways as nodes and reactions in pathways as edges;
    a memory; and
    a processor coupled with the memory, the processor configured to perform the steps of:
        connecting the nodes and edges to create a reaction network;
        identifying a plurality of seed modules in the reaction network by using connections between the compounds in the pathways as the nodes and the reactions in the pathways as the edges, wherein the plurality of seed modules are defined based on edge connectivity in the public database;
        creating a tag map for each of the identified seed modules represented by a module ID, wherein the tag map is a multidimensional module map containing a plurality of tag map values, wherein the plurality of tag map values comprising an alphanumeric ID for the seed module, a name string identifier for pathway module, a reactant string identifier for source reactant, a product string identifier for target product, a metabolism string identifying a type of reaction and a protein family list;
        providing a list of six queries to a biomedical literature search engine, wherein the list of six queries are generated using the plurality of tag map values, wherein the list of six queries comprise a metabolism string+reactant string+product string, a metabolism string+reactant string, a metabolism string+product string, a metabolism string+reactant string+product string+'gene cluster', a metabolism string+reactant string+product string+'bacteria' and a metabolism string+reactant string+product string+'operon', wherein the six queries are generated for each of the alphanumeric ID, wherein the biomedical literature search engine provides search output as six lists (L1 to L6) of publication IDs corresponding to the six queries;
    sorting each of the six lists based on relevance to each query and selecting a predefined number of entries from each list to create a new list;
        creating a pre-calculated mapping of the publication IDs to corresponding organisms to generate a hash 'PO' with the publication IDs as key and organism names as 'values' and identifying the organism names corresponding to each publication ID from the new list by using the hash PO;
        creating an organism map by storing the organism names corresponding to the each publication ID in the new list thereby mapping the module ID with the corresponding organisms;
    creating a genome protein family map and a seed module protein family map using the organism map, wherein the creation of the genome protein family map comprises:
        performing Hidden Markov Model (HMM) based protein domain search on a protein database comprising protein sequences of genome;
        obtaining protein family (Pfams) list corresponding to each genome 'G' and a mapping hash 'GP' created with 'key' as 'genome name' and 'value' as the Pfam list; and
    wherein the creation of seed module protein family map comprises the steps of:
        obtaining a list for each edge of the reaction network created for each of the plurality of seed modules corresponding to a protein family;
        obtaining a corresponding protein family IDs from the metabolic reaction knowledgebase; and
        updating the protein family list from the plurality of tag map values with the protein family IDs so obtained;
    refining the identified plurality of seed modules using the genome protein family map and the seed module protein family map to generate a new tag map, wherein the refining comprises:
        obtaining the protein family list for each of the plurality of seed modules and creating a location array for each protein family list for each of the plurality of seed modules using the mapping hash 'GP' as a reference;
        merging all the location arrays into a single location array 'SLA' keeping only unique locations;
        identifying location clusters from the 'SLA' separating a predefined number of genomes;
        assigning each cluster a new module and creating the new tag map for the new module ID using the new module ID as a key and two values including the protein family list corresponding to the new module ID and organism list corresponding to the new module ID;
    creating a matrix of genomes against pathways and a matrix of genomes against protein domains using genome protein family map and the new tag map, wherein the matrix of genomes against pathways and the matrix of genomes against the protein domains are mapped, wherein the genome protein family map is used to search for the organisms which have all the protein family (Pfams) of the module in a gene context, wherein the gene context refers to relative order of constituent genes of the pathway in the genome organized into groups of gene-clusters, and wherein the genomes and the protein domains are obtained from the genome protein family map;
    calculating a domain probability of occurrence of the domain in the refined seed module in the genome; and
    calculating a domain presence score, a domain skew index and a module probability score using the domain probability score to predict the functional potential of the pathways in the genome, wherein the functional potential of the pathways in the genome is used to gain insights in understanding at least one of human physiology, metabolism, nutrition and immune function.

6. A non-transitory computer-readable medium having embodied thereon a computer program for estimation of functional potential of pathways in genomes and metagenomes, the method comprising:

extracting a metabolic reaction knowledgebase from a public database, wherein the metabolic reaction knowledgebase comprises of compounds in pathways as nodes and reactions in pathways as edges;

connecting the nodes and edges to create a reaction network;

identifying a plurality of seed modules in the reaction network by using connections between the compounds in the pathways as the nodes and the reactions in the pathways as the edges, wherein the plurality of seed modules are defined based on edge connectivity in the public database;

creating a tag map for each of the identified seed modules represented by a module ID, wherein the tag map is a multidimensional module map containing a plurality of tag map values, wherein the plurality of tag map values comprising an alphanumeric ID for the seed module, a name string identifier for pathway module, a reactant string identifier for source reactant, a product string identifier for target product, a metabolism string identifying a type of reaction and a protein family list;

providing a list of six queries to a biomedical literature search engine, wherein the list of six queries are generated using the plurality of tag map values, wherein the list of six queries comprise a metabolism string+reactant string+product string, a metabolism string+reactant string, a metabolism string+product string, a metabolism string+reactant string+product string+'gene cluster', a metabolism string+reactant string+product string+'bacteria' and a metabolism string+reactant string+product string+'operon', wherein the six queries are generated for each of the alphanumeric ID, wherein the biomedical literature search engine provides search output as six lists (L1 to L6) of publication IDs corresponding to the six queries;

sorting each of the six lists based on relevance to each query and selecting a predefined number of entries from each list to create a new list;

creating a pre-calculated mapping of the publication IDs to corresponding organisms to generate a hash 'PO' with the publication IDs as key and organism names as 'values' and identifying the organism names corresponding to each publication ID from the new list by using the hash PO;

creating an organism map by storing the organism names corresponding to the each publication ID in the new list thereby mapping the module ID with the corresponding organisms;

creating a genome protein family map and a seed module protein family map using the organism map, wherein the creation of the genome protein family map comprises:

performing Hidden Markov Model (HMM) based protein domain search on a protein database comprising protein sequences of genome;

obtaining protein family (Pfams) list corresponding to each genome 'G' and a mapping hash 'GP' created with 'key' as 'genome name' and 'value' as the Pfam list; and wherein the creation of seed module protein family map comprises the steps of:

obtaining a list for each edge of the reaction network created for each of the plurality of seed modules corresponding to a protein family;

obtaining a corresponding protein family IDs from the metabolic reaction knowledgebase; and updating the protein family list from the plurality of tag map values with the protein family IDs so obtained;

refining the identified plurality of seed modules using the genome protein family map and the seed module protein family map to generate a new tag map, wherein the refining comprises:

obtaining the protein family list for each of the plurality of seed modules and creating a location array for each protein family list for each of the plurality of seed modules using the mapping hash 'GP' as a reference;

merging all the location arrays into a single location array 'SLA' keeping only unique locations;

identifying location clusters from the 'SLA' separating a predefined number of genomes;

assigning each cluster a new module and creating the new tag map for the new module ID using the new module ID as a key and two values including the protein family list corresponding to the new module ID and organism list corresponding to the new module ID;

creating a matrix of genomes against pathways and a matrix of genomes against protein domains using genome protein family map and the new tag map, wherein the matrix of genomes against pathways and the matrix of genomes against the protein domains are mapped, wherein the genome protein family map is used to search for the organisms which have all the protein family (Pfams) of the module in a gene context, wherein the gene context refers to relative order of constituent genes of the pathway in the genome organized into groups of gene-clusters, and wherein the genomes and the protein domains are obtained from the genome protein family map;

calculating a domain probability of occurrence of the domain in the refined seed module in the genome; and calculating a domain presence score, a domain skew index and a module probability score using the domain probability score to predict the functional potential of the pathways in the genome, wherein the functional potential of the pathways in the genome is used to gain insights in understanding at least one of human physiology, metabolism, nutrition and immune function.

* * * * *